(12) United States Patent
Kim et al.

(10) Patent No.: US 11,752,210 B2
(45) Date of Patent: Sep. 12, 2023

(54) SENSITIZING COMPOSITION USING ELECTROMAGNETIC WAVES FOR THERMAL THERAPY OF CANCERS, AND CANCER THERAPY USING SAME

(71) Applicant: JINIS CO., LTD., Jeollabuk-do (KR)

(72) Inventors: Hyeon Jin Kim, Jeollabuk-do (KR); Seong Tshool Hong, Jeonju-si (KR); Hea Jong Chung, Jeonju-si (KR); Heui Kwan Lee, Jeonju-si (KR); Hea Guk Cho, Gwangju (KR); Jae Gak Yu, Chungcheongnam-do (KR)

(73) Assignee: JINIS CO., LTD., Wanju-gun (KR)

( * ) Notice: Subject to any disclaimer, the term of this patent is extended or adjusted under 35 U.S.C. 154(b) by 0 days.

(21) Appl. No.: 17/981,080

(22) Filed: Nov. 4, 2022

(65) Prior Publication Data

US 2023/0079782 A1 Mar. 16, 2023

Related U.S. Application Data

(60) Division of application No. 17/219,479, filed on Mar. 31, 2021, now abandoned, which is a continuation of application No. 15/029,726, filed as application No. PCT/KR2014/009641 on Oct. 14, 2014, now abandoned.

(30) Foreign Application Priority Data

| Oct. 16, 2013 | (KR) | 10-2013-0123051 |
| Aug. 21, 2014 | (KR) | 10-2014-0109008 |

(51) Int. Cl.

| A61K 41/00 | (2020.01) |
| A61K 38/40 | (2006.01) |
| A61K 33/06 | (2006.01) |
| A61K 33/24 | (2019.01) |
| A61K 33/26 | (2006.01) |
| A61K 45/06 | (2006.01) |
| A61N 5/02 | (2006.01) |
| A61N 5/06 | (2006.01) |
| A61N 5/10 | (2006.01) |

(52) U.S. Cl.
CPC .......... *A61K 41/0052* (2013.01); *A61K 33/06* (2013.01); *A61K 33/24* (2013.01); *A61K 33/26* (2013.01); *A61K 38/40* (2013.01); *A61K 45/06* (2013.01); *A61N 5/02* (2013.01); *A61N 5/062* (2013.01); *A61N 2005/0659* (2013.01); *A61N 2005/0661* (2013.01); *A61N 2005/0662* (2013.01); *A61N 2005/1098* (2013.01)

(58) Field of Classification Search
None
See application file for complete search history.

(56) References Cited

U.S. PATENT DOCUMENTS

| 4,569,836 A | 2/1986 | Gordon |
| 7,754,702 B2 | 7/2010 | Helenek et al. |
| 9,333,189 B2 | 5/2016 | Head et al. |
| 2009/0181048 A1 | 7/2009 | Kamei et al. |
| 2013/0090591 A1* | 4/2013 | Ferrara ............... A61K 31/704 604/20 |
| 2013/0158293 A1 | 6/2013 | Chibazakura et al. |
| 2013/0197295 A1 | 8/2013 | Krishnan et al. |
| 2013/0336897 A1 | 12/2013 | Wolf et al. |

FOREIGN PATENT DOCUMENTS

| EP | 1 704 870 A1 | 9/2006 |
| JP | 1-235851 A | 9/1989 |
| JP | 2006-298897 A | 11/2006 |
| JP | 2009-233175 A | 10/2009 |
| JP | 2011-520791 A | 7/2011 |
| KR | 10-2013-0079492 A | 7/2013 |
| WO | 2004108165 A2 | 12/2004 |
| WO | 2009/013630 A2 | 1/2009 |
| WO | 2012/036978 A1 | 3/2012 |
| WO | 2012/177875 A1 | 12/2012 |

OTHER PUBLICATIONS

International Searching Authority, International Search Report of PCT/KR2014/009641 dated Jan. 27, 2015.
Japanese Patent Office, Communication dated Dec. 20, 2016, issued in counterpart JP Application No. 2016-524018.
Russian Patent Office; Communication dated May 17, 2017 in counterpart application No. 2016118565.
European Patent Office, Communication dated Jul. 5, 2017 in counterpart European application No. 14853591.7.
Cheng,L-C., et al., "Targeting polymeric fluorescent nanodiamond-gold/silver multi-functional nanoparticles as a light-transforming hyperthermia reagent for cancer cells", The Royal Society of Chemistry, Nanoscale, vol. 5, No. 9, 2013, pp. 3931-3940 (10 pages).

(Continued)

*Primary Examiner* — Danah Al-Awadi
(74) *Attorney, Agent, or Firm* — Sughrue Mion, PLLC

(57) ABSTRACT

Disclosed are a sensitizing composition for thermal cancer therapy using electromagnetic waves and a method of treating cancer using the composition. The sensitizing composition includes a metal ion, a metal ion-bound material, metal ion-noncovalently bound apotransferrin (transferrin), or a metal ion-noncovalently bound apotransferrin derivative. The sensitizing composition enables selective delivery of the metal ion to tumorous tissue when administered in vivo, and thus the generation of heat in tumorous tissue in which the metal ion accumulates is increased upon thermal cancer therapy using electromagnetic waves, thereby maximizing efficacy of thermal cancer therapy using electromagnetic waves in treating cancer. Thermal therapy using the sensitizing composition effectively treats cancer without pain or side effects and is thus expected to be widely useful in anticancer treatment as monotherapy, and/or in combination with chemotherapy, radiation therapy, or a combination thereof, ultimately increases the potential to cure cancer.

4 Claims, 9 Drawing Sheets

(56) References Cited

OTHER PUBLICATIONS

Yang, C., et al., "Surface plasmon-enhanced Ag/CuS nanocomposites or cancer treatment", Cancer Nanotechnology, vol. 4, No. 4-5, 2013, pp. 81-89 (9 pages).
Bhattacharyya, S., et al., "Inorgnaic Nanoparticles in Cancer Therapy", Pharmaceutical Research, vol. 28, No. 2, 2010, pp. 237-259 (23 pages).
Japanese Patent Office; Communication dated Sep. 19, 2017 in counterpart Japanese application No. 2016-524018.

\* cited by examiner

[Fig. 1]
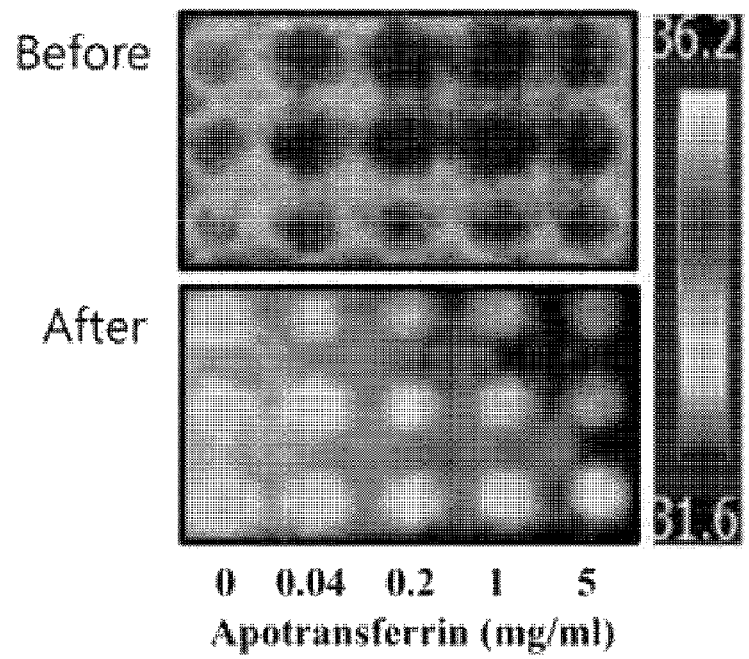
[Fig. 2]
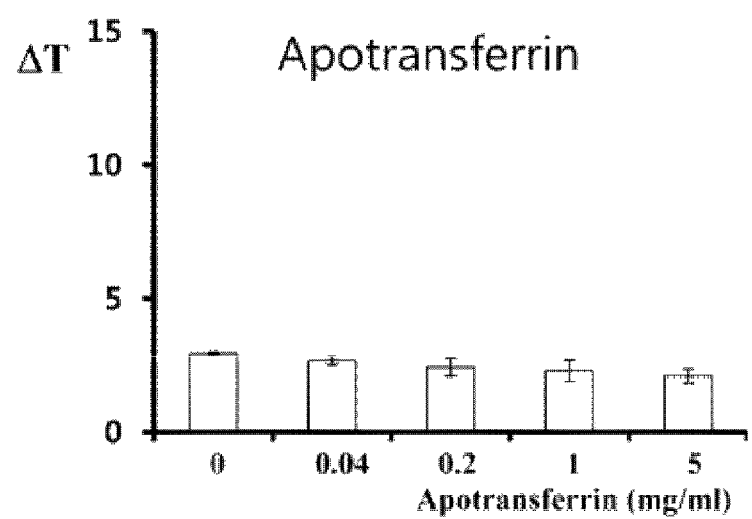

[Fig. 3]
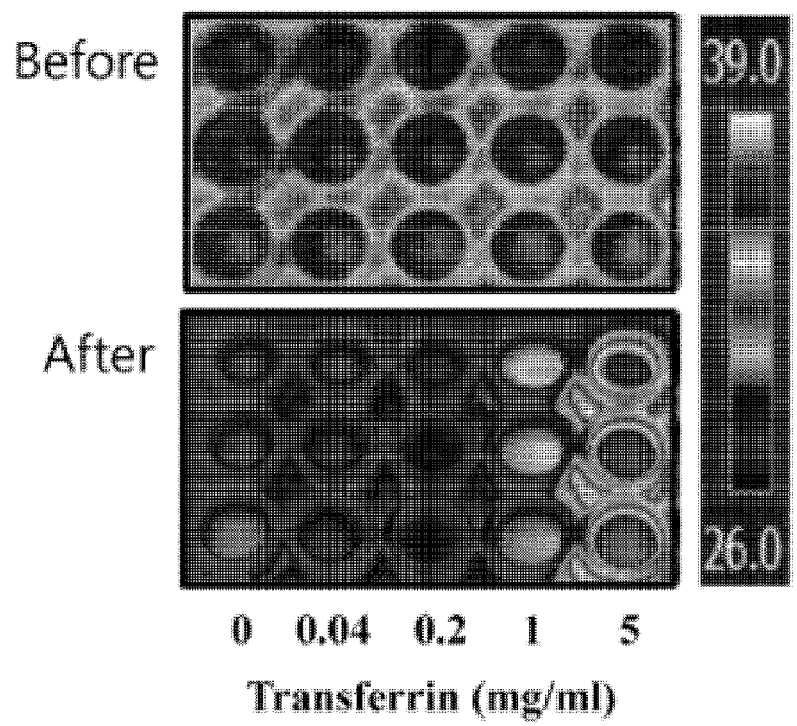
[Fig. 4]
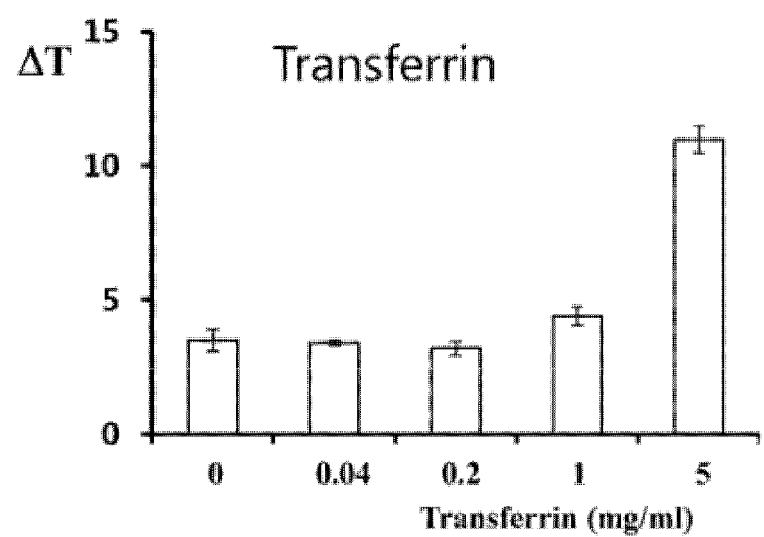

[Fig. 5]
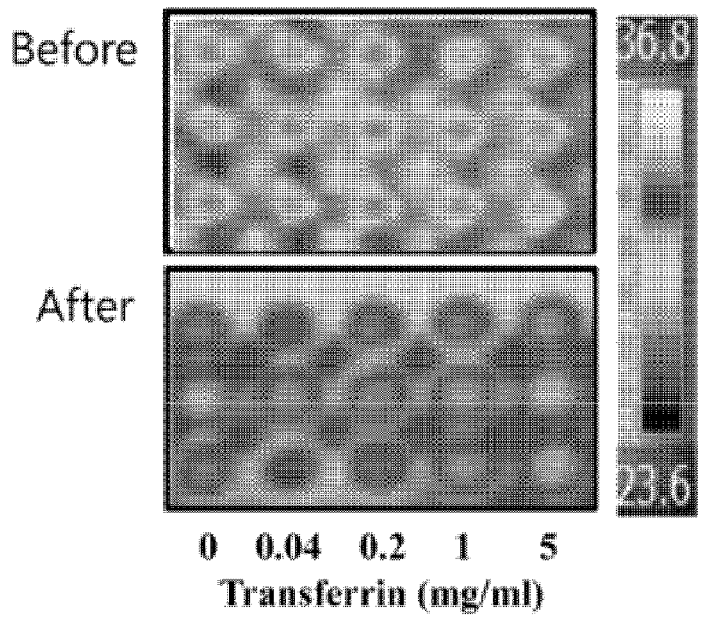
[Fig. 6]
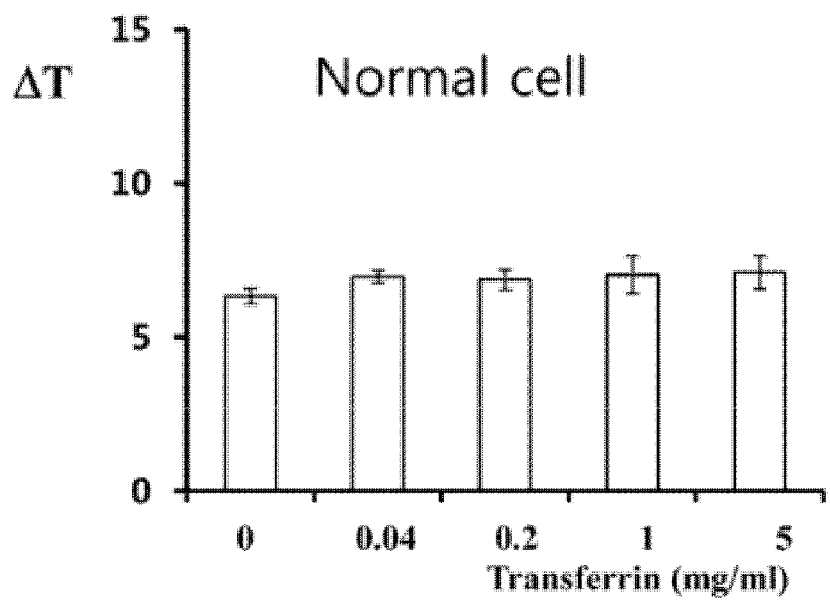

[Fig. 7]
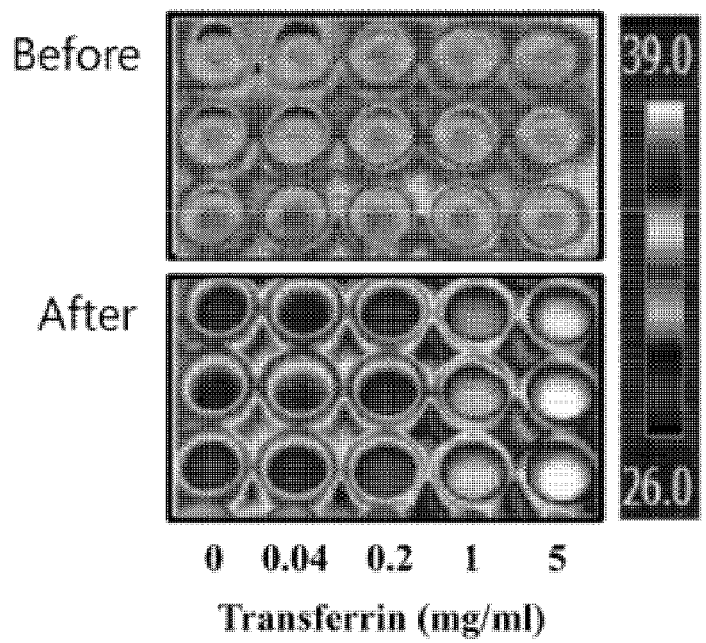
[Fig. 8]
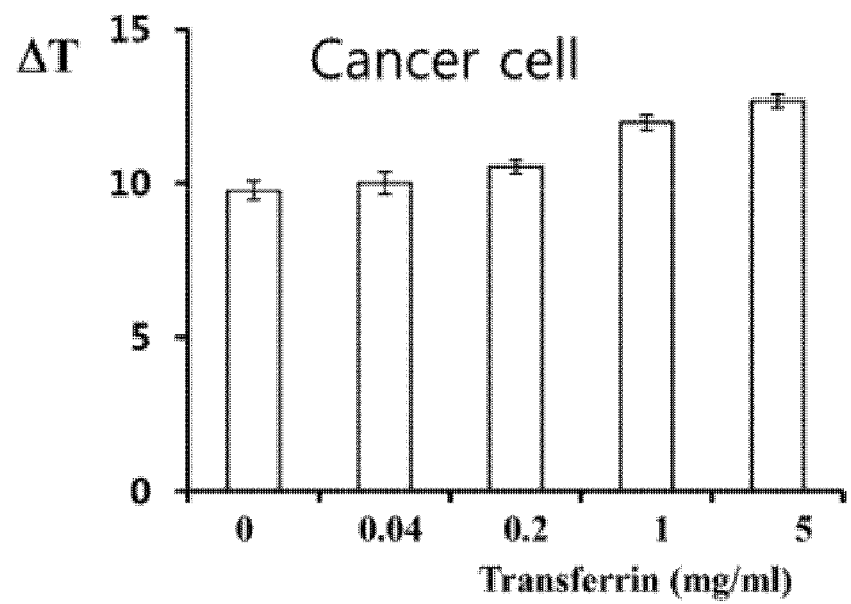

[Fig. 9]
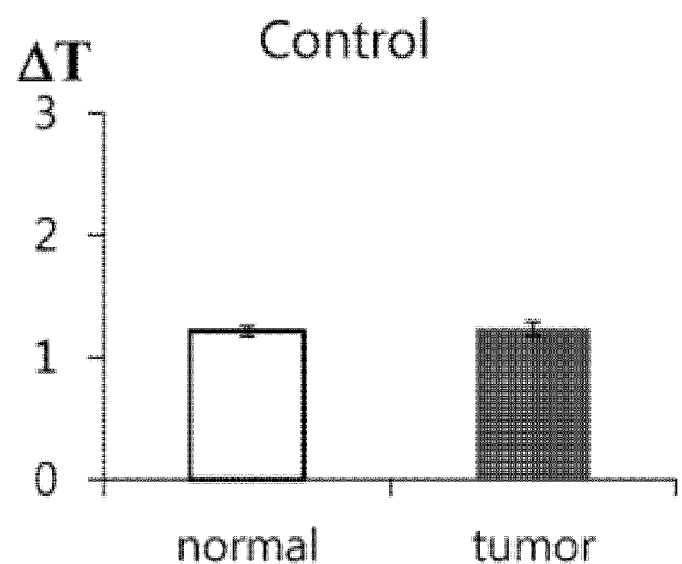
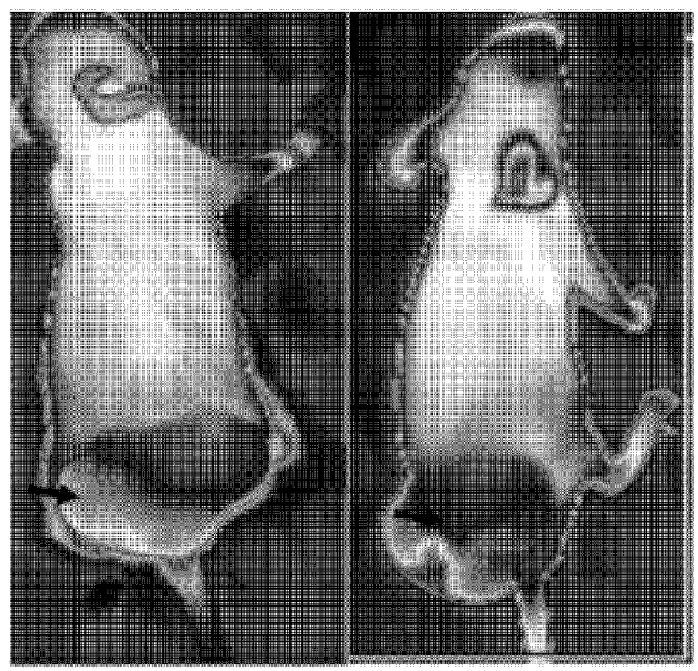

[Fig. 10]
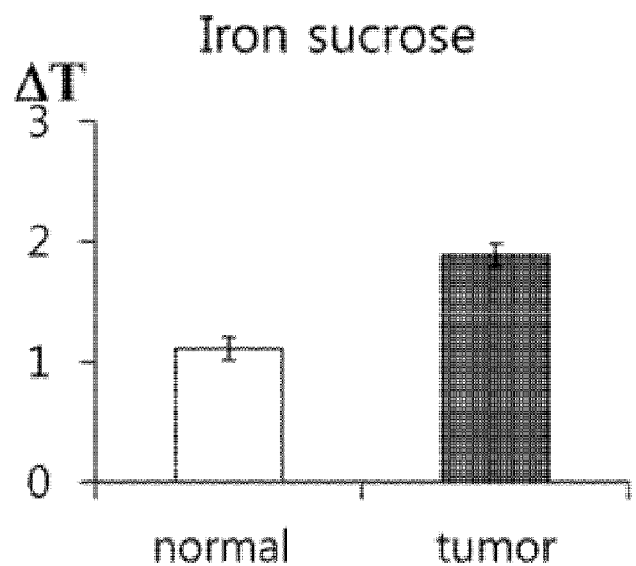
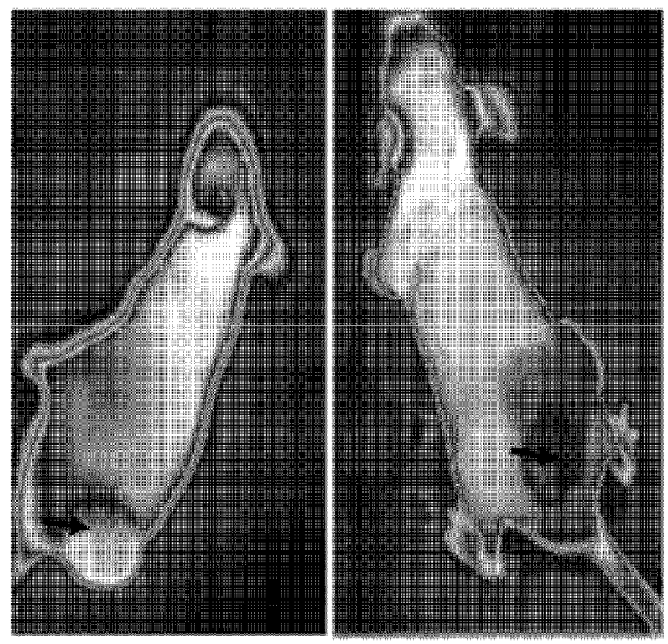

[Fig. 11]
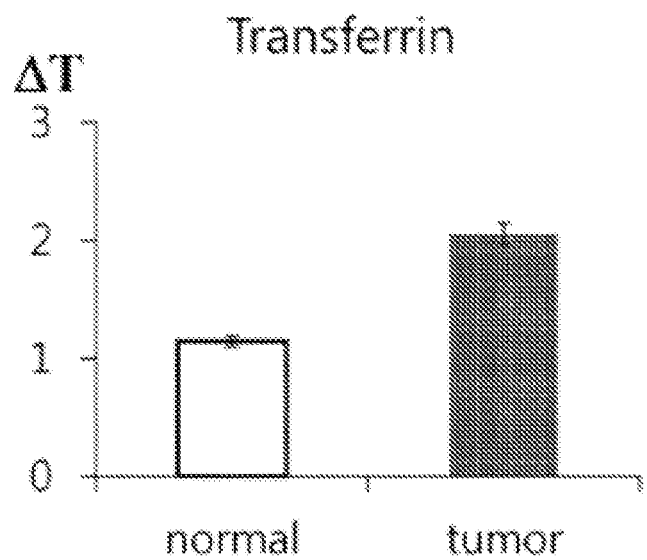
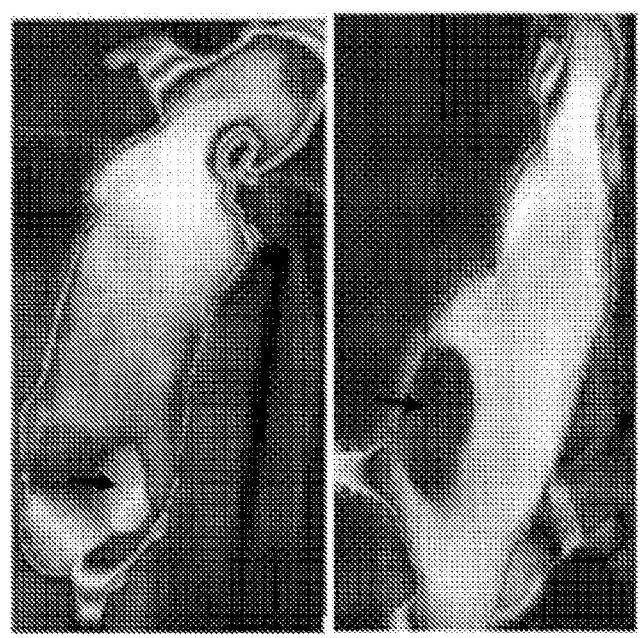

[Fig. 12]
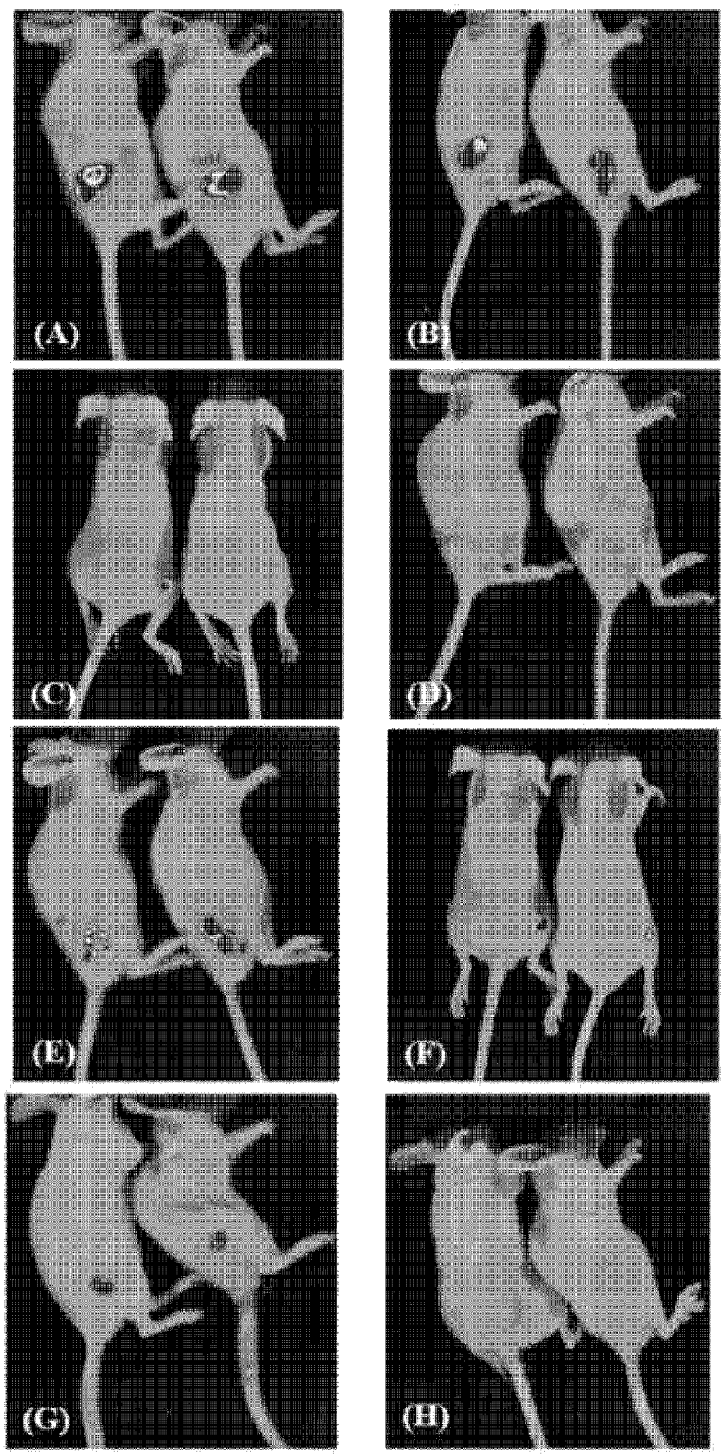

[Fig. 13]
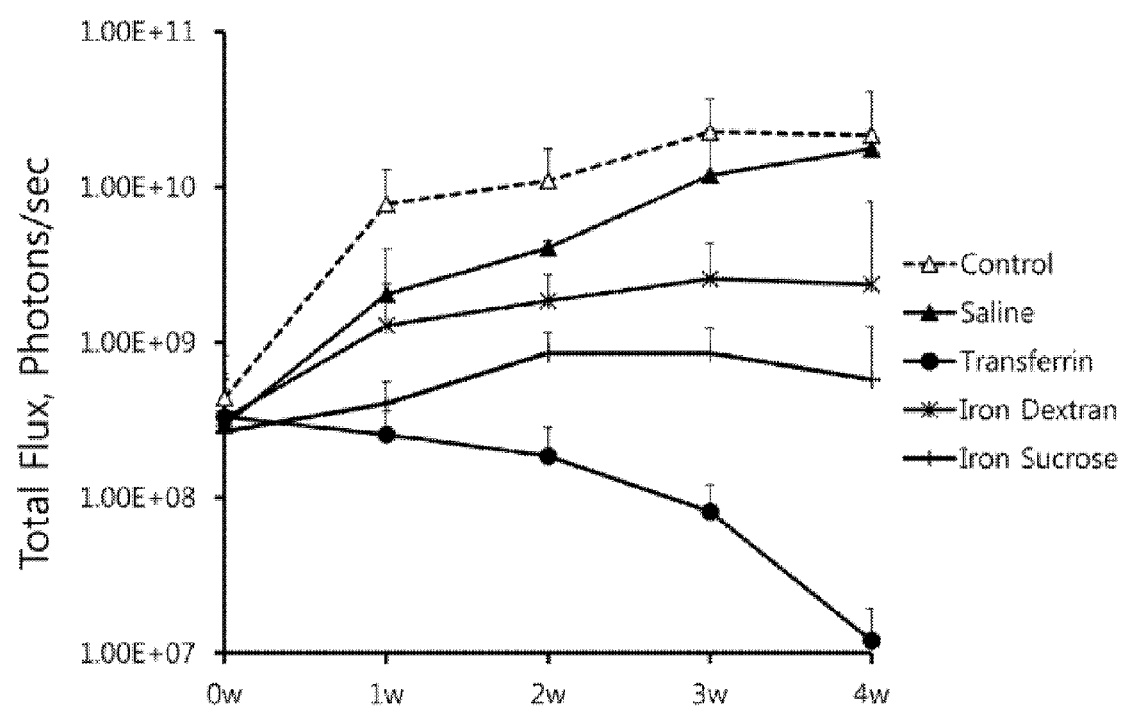

SENSITIZING COMPOSITION USING ELECTROMAGNETIC WAVES FOR THERMAL THERAPY OF CANCERS, AND CANCER THERAPY USING SAME

CROSS REFERENCE TO RELATED APPLICATIONS

This is a Divisional of U.S. application Ser. No. 17/219,479 filed Mar. 31, 2021, which is a Continuation of U.S. application Ser. No. 15/029,726, filed Apr. 15, 2016, which is a National Stage of International Application No. PCT/KR2014/009641 filed Oct. 14, 2014, claiming priority based on Korean Patent Application No. 10-2013-0123051 filed Oct. 16, 2013 and Korean Patent Application No. 10-2014-0109008 filed Aug. 21, 2014, the contents of all of which are incorporated herein by reference in their entirety.

TECHNICAL FIELD

The present invention relates to a sensitizing composition for thermal cancer therapy using electromagnetic waves and a method of treating cancer using the same and, more particularly, to a sensitizing composition for thermal cancer therapy, which is able to increase sensitivity upon treatment of cancer using electromagnetic waves, and a method of treating cancer using the same.

BACKGROUND ART

With recent advancements in modern medicine, the early diagnosis of cancer has become possible, and a variety of cancer treatment methods, such as surgical therapy, radiation therapy and anticancer drug therapy, have been developed, and thus the likelihood of overcoming cancer has come to the fore. However, the cancer treatment methods that have been developed to date are merely used simply to prolong the life of cancer patients, rather than to fundamentally treat cancer. Hence, there is an urgent need to develop cancer therapy that is effective and has low side effects.

Typical examples of cancer therapy include surgical therapy, anticancer drug therapy, and radiation therapy. Surgery therapy is the best for early cancer treatment but it is difficult to expect good therapeutic effects in the case where the cancer spreads to other tissues.

Radiation therapy and anticancer drug therapy have low cancer treatment effects and have an effect on normal tissue, being known to cause a variety of side effects, such as gastrointestinal disorders, immune dysfunction, loss of appetite, general weakness, hair loss, etc. In order to alleviate the limitations of such conventional cancer therapy, various kinds of cancer treatment methods are currently being developed. Particularly useful is thermal anticancer therapy (Wust et al., The Lancet Oncology, 2002, 3:487-497).

Cancer cells are inherently characterized in that the thermal adaptability thereof is considerably lower than that of normal cells (Wust et al., The Lancet Oncology, 2002, 3:487-497). Thermal anticancer therapy is a method of treating cancer by raising the temperature of tumorous tissue and the ambient temperature thereof to 42° C. or higher, based on the poor thermal adaptability of cancer cells. When the temperature of tumorous tissue is elevated during thermal anticancer therapy, nearby normal cells are resistant to thermal impact and may thus survive, but cancer cells, having low thermal adaptability, are not adaptable to high temperatures and are thus killed. In order to increase the temperature of tumorous tissue during the thermal anticancer therapy, various methods, including the use of ultrasonic waves, heat transfer through contact, and use of electromagnetic waves, have been developed. However, the most typical and effective method among currently useful thermal anticancer therapies is thermal cancer therapy using electromagnetic waves to generate heat in tumorous tissue (EP Patent Application Publication No. 2174689, U.S. Pat. No. 4,323,056, International Patent Application No. 2002-172198, Korean Patent No. 1125200, International Patent Application No. 2010-043372, and International Patent Application No. 2009-013630).

Electromagnetic waves are waves that are generated while an electric field and a magnetic field are varied over time, and examples of the electromagnetic waves include gamma rays, X-rays, UV rays, visible light, IR rays, microwaves, radio waves, etc. When electromagnetic waves pass through a polar material, electromagnetic waves stimulate the molecular motion of the polar material to thus generate heat. Although all kinds of electromagnetic waves may be utilized in thermal anticancer therapy, a radio frequency of 13.56 MHz is the most commonly used in "thermal cancer therapy using electromagnetic waves".

The electromagnetic waves used for "thermal cancer therapy using electromagnetic waves" generate heat through dielectric heating. Water molecules, which constitute most of the human body, have dipole moments through asymmetrical bonding between oxygen and hydrogen atoms. Because of the dipole moments of water molecules, water molecules that are exposed to electromagnetic waves upon "thermal cancer therapy using electromagnetic waves" repeatedly undergo molecular rotation a number of times proportional to a frequency of electromagnetic waves, whereby the molecules are pulled or pushed to each other or collide with each other, consequently generating heat in the tissue exposed to the electromagnetic waves. If electromagnetic waves are radiated only on cancer cells, cancer cells may be efficiently killed due to the low thermal adaptability of cancer cells. However, it is impossible to radiate the electromagnetic waves only on cancer cells, other than normal cells, owing to the structural and physical limitations of the human body. Accordingly, limitations are imposed on the treatment of cancer through physical radiation of, for example, electromagnetic waves onto tumorous tissue, and the therapeutic effects of "thermal cancer therapy using electromagnetic waves" are not high, compared to anticancer drug therapy or radiation therapy, and thus "thermal cancer therapy using electromagnetic waves" is not used alone but is merely used as an aid to anticancer drug therapy or radiation therapy.

In order to increase the therapeutic effect of thermal cancer therapy using electromagnetic waves, a sensitizer for thermal therapy is administered, and then thermal cancer therapy is performed using electromagnetic waves.

To date, sensitizers for thermal therapy include nanoparticles based on metal components such as gold, iron oxide, etc. (International Patent Application Nos. 2009-091597, 2012-036978, and 2012-177875, U.S. Pat. No. 6,541,039, and Korean Patent No. 0802139). Metals efficiently respond to electromagnetic waves to thus generate heat. Therefore, cancer treatment efficacy is deemed to be maximized when electromagnetic waves are radiated under the condition that the metal component is controlled not to accumulate in normal cells but to accumulate only in cancer cells. However, techniques enabling the selective delivery of the metal component only to tumorous tissue have not yet been developed, and thus the concept of "thermal cancer therapy using electromagnetic waves" is not realized thereby.

Metal nanoparticles, such as those of gold or iron oxide, have no tumorous tissue selectivity and accumulate in normal tissue as well as tumorous tissue. As such, the use of electromagnetic waves causes damage to normal tissue due to heat generation at all the portions where such nanoparticles are located. Furthermore, metal nanoparticles are neither degraded nor released in vivo, undesirably decreasing safety. Such metal-based nanoparticles are thus unsatisfactory for commercial use as a sensitizer for thermal therapy, and thus sensitizers for thermal therapy have not yet been commercialized anywhere in the world.

Various kinds of metal components exist in vivo as essential constituents in all living things, including humans. The metal component does not exist in vivo as metal itself, but is mainly present in ionic form, and performs various functions necessary for life support. Metal ions, such as magnesium, manganese, iron, etc., are essential nutrients that must be taken in for the maintenance of life. Metal ions absorbed in vivo are not independently present in the blood but exist in the state of being bound to a protein for delivering a metal ion, known as transferrin. Apotransferrin, which is not bound to any iron ion, is converted into monoferric transferrin when bound to one iron ion, and into diferric transferrin or holo-transferrin when bound to two iron ions. About 70% of the transferrin protein in human serum exists in the form of apotransferrin, which is not bound to any iron ion, and the remaining transferrin, about 30%, is known to be iron ion-bound apotransferrin, that is, monoferric transferrin or diferric transferrin (Huebers et al., 1981, Proc. Natl. Acad. Sci. 78:2572-2576). Accordingly, a large amount of apotransferrin capable of being bound anytime to metal ions fed from outside is present in the blood.

"Metal ion-noncovalently bonded apotransferrin" (transferrin) is transported through the blood, is coupled with a transferrin receptor, and is then introduced into the cells through endocytosis to deliver a metal ion, whereby transferrin, from which the metal ion is removed, that is, apotransferrin, is extracted from the cells through exocytosis and is then bound again to a metal ion. In this way, the metabolic process cycles. The transferrin receptor, which plays the important function of delivering the metal ion, bound to transferrin, into the cells, is known to exhibit over-expression in cancer cells compared to normal cells.

Since cancer cells absolutely need enzymes that include metal ions as co-enzymes during cell metabolism, they strongly absorb any metal ion present in the blood. As described above, the metal ion is not independently present in the blood but is present in the form of being bound to transferrin, and thus, the metal ion which is absorbed by the cancer cells in the blood is substantially a metal ion bound to transferrin. Iron, which is transported by transferrin, is used as an essential cofactor and regulatory factor for a variety of enzymes that perform various functions of dividing cells, such as DNA synthesis, cell division cycles, metabolism, etc. Since these enzymes are considered important during the metabolic process, cancer cells require a large amount of iron in order to maintain the rapid metabolic process, thus predominantly receiving transferrin. Specifically, cancer cells require more iron than normal cells, and the receptor for transferrin, which is a protein for delivering iron, is over-expressed. As a result, transferrin in the blood is efficiently delivered into tumorous tissue, which is called cancer targetability of transferrin. Anticancer nanoparticles to which transferrin is attached using the cancer targetability of transferrin have been disclosed (U.S. Serial No. 2009-0181048, and EP Patent Application Publication Nos. 2216341 and 1369132).

Although transferrin has been utilized as a cancer targeting material, there is no report on the use of "metal ion-noncovalently bound apotransferrin" (transferrin) as a sensitizer for thermal therapy.

Therefore, the present inventors, having recognized the characteristics of cancer cells, which strongly absorb metal ions in the blood, and the characteristics of metal, which responds sensitively to electromagnetic waves, have found that when a metal ion, rather than a metal or metal compound, is administered to cancer patients as a sensitizer for thermal cancer therapy using electromagnetic waves, 1) the metal ion injected into the blood is bound to excess apotransferrin in the blood to form transferrin; 2) the metal ion-noncovalently bound apotransferrin is selectively delivered to cancer cells by means of the transferrin receptor, which is over-expressed in cancer cells, and thus the concentration of the metal ion delivered by transferrin is increased in cancer cells; and 3) thermal therapy using electromagnetic waves intensively generates heat in the cancer cells in which the metal ion accumulates, thus minimizing damage to normal cells and intensively killing only the cancer cells, thereby culminating in the present invention. Also, the present inventors have found that even when the "metal ion-noncovalently bound apotransferrin" is administered to cancer patients as a sensitizer for thermal therapy and "thermal cancer therapy using electromagnetic waves" is performed, the efficacy of cancer treatment may be drastically improved as described above, thus culminating in the present invention.

DISCLOSURE

Technical Problem

Therefore, an object of the present invention is to provide a sensitizing composition for thermal cancer therapy, a thermal cancer therapy kit including the same, and a method of treating cancer using the same, in which the sensitizing composition enables the metal ion to be selectively delivered only to tumorous tissue, thus maximizing the generation of heat only in the tumorous tissue upon "thermal cancer therapy using electromagnetic waves" to thereby treat cancer.

Technical Solution

In order to accomplish the above object, the present invention provides a sensitizing composition for thermal cancer therapy using electromagnetic waves, comprising a sensitizer.

In the present invention, the sensitizer may be selected from the group consisting of a metal ion, a metal ion-bound material, metal ion-noncovalently bound apotransferrin, and a metal ion-noncovalently bound apotransferrin derivative.

In the present invention, the metal ion may be selected from the group consisting of an iron ion, a manganese ion, a zinc ion, a copper ion, a magnesium ion, a bismuth ion, a ruthenium ion, a titanium ion, a gallium ion, an indium ion, a vanadyl ion, a chromium ion, an aluminum ion, and a plutonium ion.

In the present invention, the metal ion-bound material may be configured such that the metal ion is noncovalently bound to a binding material selected from the group consisting of dextran, sucrose, gluconate, sorbitol, polysaccharide, carboxymaltose, ferumoxytol, isomaltoside, citrate, chloride, sulfate, fumarate, maltose, starch, cellulose, and albumin.

In the present invention, the apotransferrin or the apotransferrin derivative may be a human- or mammal-derived serum protein or recombinant protein.

In the present invention, the sensitizer may have a concentration of 0.01 to 100 mg/ml.

In the present invention, the sensitizing composition may further comprise a pharmaceutically acceptable carrier.

In addition, the present invention provides a thermal cancer therapy kit, comprising a sensitizing composition for thermal cancer therapy using electromagnetic waves and a device for applying electromagnetic waves.

In addition, the present invention provides a method of treating cancer, comprising: (a) administering the sensitizing composition as above to an animal, thus increasing sensitivity to cancer treatment; and (b) applying electromagnetic waves.

In the present invention, the sensitizing composition may be administered in a dose of 1 to 250 mg/kg.

In the present invention, the electromagnetic waves may be selected from the group consisting of gamma rays, X-rays, UV rays, visible light, IR light, microwaves, and radio waves.

In the present invention, the method may be performed in combination with any one or more selected from the group consisting of chemotherapy, radiation therapy, biological therapy, immunotherapy, and photodynamic therapy.

Advantageous Effects

According to the present invention, a sensitizing composition for thermal cancer therapy has cancer targetability and can thus selectively deliver a metal ion to tumorous tissue. Therefore, upon thermal cancer therapy using electromagnetic waves, the generation of heat in tumorous tissue in which the metal ion accumulates is increased, thereby maximizing the efficacy of thermal cancer therapy using electromagnetic waves.

DESCRIPTION OF DRAWINGS

FIG. 1 is of images, taken by a thermal imaging camera, illustrating the temperature of an apotransferrin aqueous solution before and after the application of electromagnetic waves in Test Example 3 according to the present invention;

FIG. 2 is a graph illustrating changes in the temperature of the apotransferrin aqueous solution before and after the application of electromagnetic waves in Test Example 3 according to the present invention;

FIG. 3 is of images, taken by a thermal imaging camera, illustrating the temperature of a transferrin aqueous solution before and after the application of electromagnetic waves in Test Example 3 according to the present invention;

FIG. 4 is a graph illustrating changes in the temperature of the transferrin aqueous solution before and after the application of electromagnetic waves in Test Example 3 according to the present invention;

FIG. 5 is of images, taken by a thermal imaging camera, illustrating the temperature of transferrin-cultured normal cells before and after the application of electromagnetic waves in Test Example 3 according to the present invention;

FIG. 6 is a graph illustrating changes in the temperature of the transferrin-cultured normal cells before and after the application of electromagnetic waves in Test Example 3 according to the present invention;

FIG. 7 is of images, taken by a thermal imaging camera, illustrating the temperature of transferrin-cultured cancer cells before and after the application of electromagnetic waves in Test Example 3 according to the present invention;

FIG. 8 is a graph illustrating changes in the temperature of the transferrin-cultured cancer cells before and after the application of electromagnetic waves in Test Example 3 according to the present invention;

FIG. 9 is of images, taken by a thermal imaging camera, illustrating normal tissue and tumorous tissue (the portions indicated by the arrows) upon thermal therapy using electromagnetic waves after the administration of saline (control) to tumor xenograft mice in Example 1 according to the present invention, and also shows a graph illustrating changes in temperature (white bar: normal tissue, black bar: tumorous tissue);

FIG. 10 is of images, taken by a thermal imaging camera, illustrating normal tissue and tumorous tissue (the portions indicated by the arrows) upon thermal therapy using electromagnetic waves after the administration of a sensitizer (iron sucrose) for thermal therapy to tumor xenograft mice in Example 1 according to the present invention, and shows a graph illustrating changes in temperature (white bar: normal tissue, black bar: tumorous tissue);

FIG. 11 is of images, taken by a thermal imaging camera, illustrating normal tissue and tumorous tissue (the portions indicated by the arrows) upon thermal therapy using electromagnetic waves after the administration of a sensitizer (transferrin) for thermal therapy to tumor xenograft mice in Example 1 according to the present invention, and shows a graph illustrating changes in temperature (white bar: normal tissue, black bar: tumorous tissue);

FIG. 12 illustrates the results of bioluminescence imaging of the size of tumorous tissue of tumor xenograft mice, to which saline or metal ion-bound materials were administered and to which electromagnetic waves were then applied, in Example 1 according to the present invention ((A): nothing, (B): saline, (C): iron gluconate, (D): iron sucrose, (E): iron carboxymaltose, (F): iron dextran, (G): iron starch, and (H): transferrin); and FIG. 13 illustrates the results of bioluminescence imaging of the size of tumorous tissue of tumor xenograft mice, to which saline, iron sucrose, iron dextran and transferrin were administered and to which electromagnetic waves were then applied, in Example 1 according to the present invention.

BEST MODE

According to the present invention, the use of a material that targets tumorous tissue without toxicity or side effects as a sensitizer able to deliver a metal ion only to cancer cells is deemed to increase the tumorous tissue selectivity and efficacy of "thermal cancer therapy using electromagnetic waves" in treating cancer.

Specifically, a bio-derived material, which only targets tumorous tissue and exhibits no toxicity, is used to deliver a metal ion not to normal cells but to cancer cells so that the metal ion concentration of the cancer cells is increased, after which "thermal cancer therapy using electromagnetic waves" is performed, thereby maximizing cancer treatment efficacy.

Therefore, in the present invention, "metal ion-noncovalently bound apotransferrin" (transferrin) was intravenously administered to a tumor xenograft mouse model as a sensitizer for "thermal cancer therapy using electromagnetic waves", after which electromagnetic waves were applied. Consequently, (1) transferrin is selectively delivered to cancer cells, rather than normal cells, by means of a transferrin receptor that is over-expressed in cancer cells; (2) the metal ion concentration is higher in the cancer cells than in the normal cells due to the separation of the metal ion from transferrin; (3) heat generation is further increased due to the increased metal ion concentration of tumorous tissue upon the application of electromagnetic waves; (4) the death of cancer cells is increased due to the generated heat, ultimately maximizing the efficacy of thermal cancer therapy using electromagnetic waves.

Also, in the present invention, even when a metal ion, instead of "metal ion-noncovalently bound apotransferrin" (transferrin), is administered as a sensitizer to a tumor xenograft mouse model, the metal ion introduced into the blood is bound to apotransferrin that is present in an excessive amount in the blood to thus form transferrin. Thus, when the metal ion is administered to cancer patients as a sensitizer for thermal therapy and thermal cancer therapy is performed using electromagnetic waves, anticancer effects equal or superior to those described above may be obtained.

Therefore, an aspect of the present invention pertains to a sensitizing composition for thermal cancer therapy using electromagnetic waves, comprising a sensitizer.

The sensitizer is used to increase cancer treatment efficacy upon thermal therapy, and amplifies the generation of heat in tumorous tissue while exhibiting targetability to tumorous tissue upon administration in vivo.

The sensitizer may be selected from the group consisting of a metal ion, a metal ion-bound material, metal ion-noncovalently bound apotransferrin, and a metal ion-noncovalently bound apotransferrin derivative.

In the present invention, examples of the metal ion may include, but are not limited to, an iron ion, a manganese ion, a zinc ion, a copper ion, a magnesium ion, a bismuth ion, a ruthenium ion, a titanium ion, a gallium ion, an indium ion, a vanadyl ion, a chromium ion, an aluminum ion, and a plutonium ion.

The metal ion-bound material is obtained by subjecting the metal ion to non-covalent bonding with any one binding material selected from the group consisting of dextran, sucrose, gluconate, sorbitol, polysaccharide, citrate, carboxymaltose, ferumoxytol, isomaltoside, maltose, starch, cellulose, chloride, sulfate, fumarate, and albumin, and may be used without limitation so long as it is useful as a drug, and examples of the metal ion-bound material may include, but are not limited to, iron dextran, iron sucrose, iron gluconate, iron carboxymaltose, iron isomaltoside, iron ferumoxytol, iron sorbitol, iron polysaccharide, ferric citrate, ferrous gluconate, ferrous sulfate, ferrous fumarate, magnesium chloride, gallium citrate, aluminum citrate, etc.

The metal ion has an electric charge and thus has polarity, that is, a dipole moment, and the molecular motion thereof is amplified upon the application of electromagnetic waves, thereby generating heat. Hence, the metal ion, rather than the metal itself, has sensitizing properties that sensitively respond to electromagnetic waves.

When the metal ion or the metal ion-bound material, as the sensitizer, is administered to a cancer patient, 1) the metal ion injected into the blood is bound to apotransferrin that is excessively present in the blood to thus form transferrin; 2) transferrin is selectively delivered to cancer cells by a transferrin receptor that is over-expressed in cancer cells, whereby the concentration of the metal ion, delivered by transferrin, is increased in the cancer cells; 3) heat is intensively generated from the cancer cells in which the metal ion accumulates upon thermal therapy using electromagnetic waves, thus intensively killing the cancer cells while minimizing damage to normal cells.

When the metal ion-noncovalently bound apotransferrin or the metal ion-noncovalently bound apotransferrin derivate, as the sensitizer, is administered to a cancer patient, 1) "metal ion-noncovalently bound apotransferrin" (transferrin) is selectively delivered to cancer cells by the transferrin receptor, which is over-expressed in cancer cells, during circulation through the blood, and thus the concentration of the metal ion delivered by transferrin is increased in the cancer cells; 2) heat is intensively generated from the cancer cells in which the metal ion accumulates upon thermal therapy using electromagnetic waves, thus intensively killing the cancer cells while minimizing damage to normal cells.

The transferrin is a protein that is mainly distributed in the blood, and designates a metalloprotein that functions to deliver a metal ion to cells having a transferrin receptor while circulating through the blood after binding to the metal ion such as iron.

As the apotransferrin or the apotransferrin derivative, a human- or mammal-derived serum protein or recombinant protein may be used without particular limitation, so long as it targets cancer and is bound to a metal ion, such as iron, manganese, zinc, etc.

The transferrin is preferably provided in the form in which a metal ion is noncovalently bound to apotransferrin, and examples of the iron ion-bound transferrin may include monoferric transferrin, diferric transferrin, holo-transferrin, ferric acetyl transferrin and the like.

The transferrin is coupled with the transferrin receptor, which is over-expressed in cancer cells, and is then delivered into cancer cells, after which the bound metal ion is isolated in the cancer cells, thereby selectively delivering the metal ion to the tumorous tissue.

The metal ion, such as iron, manganese, zinc, etc. has a strong electric charge, and thus has polarity much stronger than the dipole moment of a water molecule. When the metal ion, having strong polarity, is exposed to electromagnetic waves, the molecular motion thereof is amplified, thus maximizing the generation of heat.

When the transferrin is administered to a cancer patient, 1) transferrin is selectively delivered to cancer cells, rather than normal cells, by means of the transferrin receptor, which is over-expressed in cancer cells; 2) the concentration of the metal ion in the cancer cells, rather than in the normal cells, is increased due to the separation of the metal ion from the transferrin; 3) the generation of heat is further increased by the metal ion at a higher concentration in tumorous tissue upon the application of electromagnetic waves; 4) the death of the cancer cells is raised due to the generated heat, thus exhibiting cancer treatment efficacy.

In the sensitizing composition for thermal cancer therapy, the concentration of the sensitizer is not particularly limited but preferably falls in the range of 0.01 to 100 mg/ml. If the concentration thereof is less than 0.01 mg/ml, the sensitizer has to be administered in an excessive amount, which is regarded as cumbersome. On the other hand, if the concentration thereof exceeds 100 mg/ml, it is difficult to prepare such a composition.

In the present invention, the sensitizing composition for thermal cancer therapy may further include a pharmaceutically acceptable carrier, a lubricant, a wetting agent, an emulsifier, a suspending agent, a preservative, etc.

In addition, another aspect of the present invention pertains to a thermal cancer therapy kit, including the sensitizing composition and a device for applying electromagnetic waves.

The sensitizing composition for thermal cancer therapy, according to the present invention, may be employed in treating a variety of cancer-related diseases, for example, gastric cancer, lung cancer, breast cancer, ovarian cancer, liver cancer, bronchial cancer, nasopharyngeal cancer, laryngeal cancer, pancreatic cancer, bladder cancer, colorectal cancer, cervical cancer, etc. and may be incorporated into the thermal cancer therapy kit that includes the device for applying electromagnetic waves.

The electromagnetic waves are waves that are generated while an electric field and a magnetic field change over time, and examples thereof may include gamma rays, X-rays, UV rays, visible light, IR rays, microwaves, radio waves, etc., and any typical device for applying electromagnetic waves may be used in the present invention.

In addition, still another aspect of the present invention pertains to a method of treating cancer, comprising: (a) administering the sensitizing composition to an animal to thus increase sensitivity to cancer treatment and (b) applying electromagnetic waves.

The sensitizing composition is preferably used by dissolving the metal ion, metal ion-bound material, metal ion-noncovalently bound apotransferrin, or metal ion-noncovalently bound apotransferrin derivative at a concentration of 0.01 to 100 mg/ml in an injectable solution, such as water, saline, etc.

In order to exhibit the effects of thermal cancer therapy using electromagnetic waves, the sensitizing composition is preferably administered in a dose of 0.1 to 50 mg/kg in the case of the metal and the metal ion-bound material, and preferably in a dose of 0.1 to 200 mg/kg in the case of the metal ion-noncovalently bound apotransferrin and the derivative thereof.

To exhibit the desired effects of thermal cancer therapy using electromagnetic waves, thermal cancer therapy using electromagnetic waves is preferably carried out within 1 to 48 hr after the administration of the sensitizing composition.

The thermal cancer therapy using electromagnetic waves may be easily performed by any known thermal treatment process. For example, treatment for 30 to 60 min using a hyperthermia system for outputting a radio frequency of 13.56 MHz is performed two times or more per week for at least four weeks.

The method of treating cancer according to the present invention may be used in conjunction or in combination with conventional anticancer therapy, thereby improving cancer treatment effects. Conventional anticancer therapy may include, for example, chemotherapy, radiation therapy, biological therapy, immunotherapy, and photodynamic therapy.

MODE FOR INVENTION

A better understanding of the present invention may be obtained through the following examples, which are set forth to illustrate, but are not to be construed as limiting the scope of the present invention, as will be apparent to those skilled in the art.

Test Example 1. Evaluation of Heat Generation Performance of Metal Ion

A metal ion for oral administration or injection to the human body is provided in the form of being bound to a salt or to a polymer, such as a carbohydrate or a protein. Examples of the salt that is bound to the metal ion may include citrate, chloride, sulfate, fumarate, etc. and the resulting bound material may be exemplified by ferrous sulfate, ferrous fumarate, ferrous gluconate, etc.

Examples of the carbohydrate that is bound to the metal ion may include saccharides, including monosaccharides, such as gluconate, disaccharides, such as sucrose and maltose, and polysaccharides, such as isomaltoside, carboxymaltose, dextran, starch, cellulose, etc., and the protein that is bound to the metal ion may be exemplified by transferrin, albumin and the like.

In the present test example, a ferrous sulfate solution, which is a metal ion/salt-bound material, was prepared, irradiated with electromagnetic waves, and measured for temperature, thereby evaluating the heat generation performance of the metal ion-bound material. Also, as the metal ion/carbohydrate-bound material, each of iron gluconate, magnesium sucrose, iron sucrose, iron isomaltoside, iron carboxymaltose, iron dextran, and iron starch complex solutions was prepared, irradiated with electromagnetic waves, and measured for temperature, thereby evaluating the heat generation performance of the metal ion-bound material.

A ferrous sulfate solution was prepared by dissolving 1 g of $FeSO_4 7H_2O$ in 10 ml of distilled water with stirring for 30 min or longer and then passing the resulting solution through a 0.22 μm filter, and was then diluted with sterile distilled water before use.

An iron gluconate solution (a sodium ferric gluconate complex) was used after dilution of a Ferrlecit product, made by Sanofi, with sterile distilled water.

A magnesium sucrose solution was prepared by dissolving 83.6 mg of $MgCl_2 H_2O$ and 150 mg of sucrose in 10 ml of distilled water with stirring for 30 min or longer and then passing the resulting solution through a 0.22 μm filter, and was then diluted with distilled water before use.

An iron sucrose solution (a ferric hydroxide sucrose complex) was prepared by dissolving 100 mg of sugar in 50 ml of distilled water at 90° C. and adding 1 ml of 5M NaOH with continuous stirring to give a sucrose aqueous solution, followed by dissolving 0.9 g of $FeCl_3$ in 50 ml of distilled water with stirring for 20 min or longer, yielding a 0.01M $FeCl_3$ aqueous solution, which was then added to the sucrose aqueous solution at 90° C., after which the pH of the resulting solution was adjusted to 12 with the dropwise addition of a 5M NaOH solution. Subsequently, reaction at 80° C. for 2 hr and centrifugation at 5,000 rpm for 5 min were performed, thus obtaining a ferric hydroxide sucrose complex, which was then washed with distilled water and dried before use.

An iron isomaltoside complex, an iron carboxymaltose complex and an iron starch complex were prepared by changing the kind of carbohydrate in the method of preparing the iron sucrose.

The metal ion-bound material was prepared at a metal ion concentration of 10 mg/ml, and 0.1 ml thereof was aliquoted per 3 wells in a 96-well plate. As such, 0.1 ml of distilled water was used as a control. The 96-well plate was exposed to an energy dose of 100 W for 5 min using a radiofrequency hyperthermia system (EHY-2000, Oncothermia). After 5 min, the temperature thereof was measured using a thermal imaging camera (E60, Korea Rental, Korea). Changes in the temperature before and after the application of electromagnetic waves are shown in Table 1 below.

TABLE 1

| | delta Temp. (° C.) |
|---|---|
| Control | 0.5 |
| Ferrous sulfate | 3.3 |
| Magnesium sucrose | 5.2 |
| Iron sucrose | 4.7 |
| Iron gluconate | 5.7 |
| Iron isomaltoside | 3.2 |
| Iron carboxymaltose | 5.8 |
| Iron dextran | 6.4 |
| Iron starch | 4.5 |

As is apparent from Table 1, when the metal ion-carbohydrate complex was irradiated at a high frequency, the temperature was increased by at least 3 to 6° C., compared to the distilled water control.

Test Example 2. Evaluation of Binding Capacity of Metal Ion to Apotransferrin

In order to evaluate binding capacity of the metal ion to apotransferrin, transferrin binding capacity (Unsaturated Iron-Binding Capacity, UIBC) was measured as follows depending on the concentration of iron ion (ferric iron, FeIII+).

Specifically, in order to prepare iron ion aqueous solutions, 3.6 g of $FeCl_3$ (Sigma Aldrich, USA) was dissolved in 400 ml of distilled water with stirring for 20 min or longer, and then the pH of the resulting solution was adjusted to 9 with continuous stirring while a 5M NaOH solution was added dropwise. When a red brownish precipitate appeared, it was stirred at 90° C. for 2 hr and was then centrifuged at 5,000 rpm for 5 min, thus obtaining a ferric hydroxide precipitate, which was then washed with distilled water and dried. The ferric hydroxide in powder form was dissolved in distilled water, yielding ferric hydroxide solutions having concentrations of 1, 10, 50, 200, and 500 g/dL. Each of the ferric hydroxide solutions at individual concentrations was added with 200 mg/dL of apotransferrin (Sigma Aldrich, USA), and mixed in a vortex for 1 min, followed by allowing the reaction between apotransferrin and iron ion to progress at 37° C. for 30 min.

In order to measure the unsaturated iron-binding capacity (UIBC) of apotransferrin, a Ferrozine colorimetric method was used. As the iron standard, ferrous chloride was prepared at a concentration of 500 g/dL in hydroxylamine hydrochloride, and the reaction solution of apotransferrin and iron was prepared as a test group. Specifically, 2 ml of 0.5M Tris buffer (pH 8) was aliquoted into all test tubes. The blank test tube was filled with 1 ml of distilled water, the standard test tube was filled with 0.5 ml of distilled water and 0.5 ml of the iron standard, and the experimental test tube was filled with 0.5 ml of the reaction solution of apotransferrin and iron ion and 0.5 ml of the iron standard, followed by mixing in a vortex for 1 min.

A spectrophotometer was zeroed at 560 nm, and the absorbance A1 was measured. Next, a 16.6 mM Ferrozine hydroxylamine hydrochloride solution was placed in an amount of 50 L in each of the test tubes, followed by mixing in a vortex for 1 min. All the test tubes were cultured at 37° C. for 10 min, and the absorbance A2 at 560 nm was measured. The absorbance $A_{560}$ at 560 nm was calculated by subtracting the absorbance A1 from the absorbance A2. The results are shown in Table 2 below.

The unsaturated iron-binding capacity (UIBC) was calculated as follows.

$$UIBC = [\text{standard conc.}] - [\text{standard conc.}] \times \text{Test } A_{560} / \text{Standard } A_{560}$$

TABLE 2

| Iron conc. (μg/dL) | 0 | 10 | 50 | 200 | 500 |
|---|---|---|---|---|---|
| UIBC (μg/dL) | 500 | 498 | 481 | 332 | 119 |

As is apparent from Table 2, in the mixed solution of iron ion and apotransferrin, the iron ion was bound to apotransferrin to thus form monoferric transferrin and diferric transferrin, whereby UIBC was decreased from 500 μg/dL to 119 μg/dL.

Test Example 3: Evaluation of Heat Generation Performance of Metal Ion-Noncovalently Bound Apotransferrin In order to evaluate the heat generation performance of "metal ion-noncovalently bound apotransferrin" (transferrin), the apotransferrin having no iron bound thereto and the apotransferrin aqueous solution having iron bound thereto were irradiated with electromagnetic waves, after which the temperatures thereof were measured. The apotransferrin (Sigma Aldrich, USA) aqueous solution having no iron ion bound thereto was diluted to concentrations of 0, 0.04, 0.2, 1 and 5 mg/ml, and 0.1 ml of each concentration thereof was aliquoted into a 96-well plate.

In order to prepare the iron ion-bound apotransferrin, the ferric hydroxide solution was reacted with apotransferrin. 3.6 g of $FeCl_3$ (Sigma Aldrich, USA) was dissolved in 400 ml of distilled water with stirring for 20 min or longer, and the pH of the resulting solution was adjusted to 9 with continuous stirring while adding a 5M NaOH solution dropwise. When a red brownish precipitate appeared, the solution was cultured at 90° C. for 2 hr with stirring and then centrifuged at 5,000 rpm for 5 min, thus obtaining a ferric hydroxide precipitate which was then washed with distilled water and dried. The ferric hydroxide in powder form was dissolved in distilled water, giving a 100 μg/dL ferric hydroxide solution. The ferric hydroxide solution was added with apotransferrin at 500 mg/dL, followed by mixing in a vortex for 1 min, after which the apotransferrin and iron ion were allowed to react at 37° C. for 30 min. The iron ion-bound apotransferrin solution was diluted to concentrations of 0, 0.04, 0.2, 1 and 5 mg/ml, and 0.1 ml of each concentration thereof was aliquoted into a 96-well plate.

The apotransferrin aqueous solution plate and the iron ion-bound apotransferrin (transferrin) aqueous solution plate were exposed to an energy dose of 100 W for 3 min using a radio-frequency hyperthermia system (EHY-2000, Oncothermia). The temperatures thereof before and after the exposure were measured using a thermal imaging camera (E60, Korea Rental, Korea). Changes in the temperature thereof are shown in FIGS. 1 to 4.

As illustrated in FIGS. 1 to 4, the temperature of the apotransferrin aqueous solution before and after the application of electromagnetic waves was maintained in the range less than 3° C. at all concentrations, whereas the temperature of the iron ion-bound apotransferrin (transferrin) aqueous solution was increased by 4.4° C. at 1 mg/ml and was increased by 10.9° C. at 5 mg/ml before and after the application of electromagnetic waves.

Test Example 4: In Vitro Evaluation of Temperature Elevation of Metal Ion-Noncovalently Bound Apotransferrin in Cancer Cells The temperature elevation by the metal ion-noncovalently bound apotransferrin was evaluated through in vitro cell testing. A cancer cell line NCI-H460 (Califer Life Sciences) in which the transferrin receptor was over-expressed was cultured, and 0.1 ml of a cell suspension at a concentration of $1 \times 10^3$ cells/ml was aliquoted into a 96-well plate and cultured in a $CO_2$ incubator at 37° C. for 12 hr. As a control, normal human cells, i.e. stromal cells, were cultured, and 0.1 ml thereof was aliquoted at a concentration of $3 \times 10^3$ cells/ml into a 96-well plate and cultured in a $CO_2$ incubator at 37° C. for 12 hr.

Each of the prepared normal cell line plate and the cancer cell line plate was added with the iron ion-bound apotransferrin (transferrin) aqueous solution at a concentration of 0, 0.04, 0.2, 1 or 5 mg/ml and then cultured in a $CO_2$ incubator at 37° C. for 4 hr. After completion of the culturing of transferrin and cells, each plate was washed with a DMEM medium, thus removing transferrin that was not introduced into the cells. Next, each plate was exposed to an energy dose of 100 W for 3 min using a radio-frequency hyperthermia system (EHY-2000, Oncothermia), and changes in the temperature were measured using a thermal imaging camera (E60, Korea Rental, Korea). The results are shown in FIGS. 5 to 8.

As illustrated in FIGS. 5 to 8, the temperature before and after the application of electromagnetic waves was maintained in the range of about 7° C. at all of the concentrations in the normal cell line, but was increased by 11.9° C. at 1 mg/ml and by 12.6° C. at 5 mg/ml in the cancer cell line.

As illustrated in FIGS. 5 to 8, when transferrin was administered and irradiated with electromagnetic waves, the temperature elevation depending on the concentration of transferrin was more selective in the cancer cell line than in the normal cell line.

Test Example 5: In Vivo Evaluation of Accumulation of Metal Ion in Tumorous Tissue In order to evaluate the accumulation of the administered metal ion in tumorous tissue through in vivo animal testing, tumor xenograft animal models were manufactured as follows. Specifically, a lung cancer cell line NCI-H460-luc2 (Califer Life Sciences) was cultured, and $5 \times 10^6$ cells were subcutaneously injected into 6- to 8-week-old female BALB/c athymic nude mice (Damul Science), and the mice were bred for about 10 days so as to grow tumorous tissue to a size of 100 $mm^3$ or more, yielding the tumor xenograft animal models.

Into the established tumor xenograft BALB/c athymic nude mice, each of the metal ion aqueous solutions of Test Example 1, that is, magnesium sucrose, iron sucrose, and iron dextran, was diluted to a concentration of 0.2 mg/ml and then intravenously injected in an amount of 0.1 ml so as to reach a dose of 1 mg/kg. After 24 hr, in order to carry out inductively coupled plasma mass spectrometry (ICP-MS), 1 g of each tissue was ground using a tissue grinder in an ice bath, and 1 ml of the ground solution was dried at −60° C. in a vacuum of 7 µmHg for 24 hr. The dried powder was added with 2 ml of 6N HCl, placed in a sealed glass reactor, and cultured in an incubator at 55° C. After 12 hr or longer, each sample was mixed in a vortex and then centrifuged at 1,000 rpm for 15 min, and the supernatant was dried with nitrogen gas, added with 1 ml of 0.01N HCl, mixed in a vortex, and then centrifuged at 1,000 rpm for 15 min. The supernatant was recovered, and the concentrations of the metal ions in the normal tissue and the tumorous tissue were measured through ICP-MS (Varian 800-MS, Palo Alto, US).

The results of ICP-MS of the concentrations of the metal ions accumulating in normal tissue and tumorous tissue after the administration of magnesium sucrose to the tumor xenograft mice are shown in Table 3 below.

TABLE 3

|  | Saline | Mg-Sucrose | Fold Increase |
| --- | --- | --- | --- |
| Tumor | 58.5 ± 24.8 | 137.7 ± 74.1 | 2.4 |
| Liver | 195.4 ± 12.6 | 145.1 ± 98.5 | 0.7 |
| Muscle | 193.5 ± 7.9 | 378.4 ± 212.3 | 2.0 |
| Spleen | 200.5 ± 2.1 | 419.2 ± 115.2 | 2.1 |
| Brain | 126.8 ± 8.7 | 113.9 ± 11.6 | 0.9 |

As is apparent from Table 3, the concentration of the magnesium ion of tumorous tissue was increased 2.4-fold or more upon the administration of magnesium sucrose.

The results of ICP-MS of the concentrations of the metal ions accumulating in normal tissue and tumorous tissue after the administration of iron sucrose to the tumor xenograft mice are shown in Table 4 below.

TABLE 4

|  | Saline | Fe-Sucrose | Fold Increase |
| --- | --- | --- | --- |
| Tumor | 13.5 ± 1.34 | 44.4 ± 3.9 | 3.29 |
| Liver | 74.5 ± 7.5 | 168.2 ± 37.3 | 2.26 |
| Kidney | 56.9 ± 7.5 | 59.8 ± 4.1 | 1.05 |
| Heart | 32.2 ± 1.8 | 99.2 ± 2.8 | 3.08 |
| Muscle | 29.5 ± 4.2 | 28.9 ± 22.1 | 0.98 |
| Stomach | 27.8 ± 3.8 | 83.1 ± 27.7 | 2.99 |
| Brain | 22.5 ± 3.7 | 46.2 ± 8.6 | 2.05 |

As is apparent from Table 4, upon the administration of iron sucrose, the concentration of the iron ion of tumorous tissue was increased 3.3-fold or more, which was higher than in main organs such as the liver, kidneys, heart, stomach, brain and the like.

The results of ICP-MS of the concentrations of metal ions accumulating in normal tissue and tumorous tissue after the administration of iron dextran to the tumor xenograft mice are shown in Table 5 below.

TABLE 5

|  | Saline | Fe-Dextran | Fold Increase |
| --- | --- | --- | --- |
| Tumor | 13.5 ± 1.34 | 46.8 ± 6.6 | 3.47 |
| Liver | 74.5 ± 7.5 | 115.5 ± 17.3 | 1.55 |
| Kidney | 56.9 ± 7.5 | 59.8 ± 15.6 | 1.05 |
| Heart | 32.2 ± 1.8 | 92.1 ± 5.8 | 2.86 |
| Muscle | 29.5 ± 4.2 | 65.7 ± 30.4 | 2.23 |
| Stomach | 27.8 ± 3.8 | 54.1 ± 12.8 | 1.95 |
| Brain | 22.5 ± 3.7 | 36.4 ± 3.4 | 1.62 |

As is apparent from Table 5, upon the administration of iron dextran, the concentration of the iron ion of tumorous tissue was increased 3.4-fold or more compared to the control, and was much higher than the extent of increase in the main organs, such as the liver, kidneys, heart, stomach, brain and the like.

Test Example 6: In Vivo Evaluation of Accumulation Capacity of Metal Ion-Noncovalently Bound Apotransferrin in Tumorous Tissue In order to evaluate the accumulation capacity of "metal ion-noncovalently bound apotransferrin" (transferrin) in tumorous tissue, the iron-bound transferrin aqueous solution was administered to the mice, after which the concentrations of the metal ions were measured in normal tissue and tumorous tissue. The iron ion-bound apotransferrin (transferrin) aqueous solution was prepared at 4 mg/ml, and 0.1 ml thereof was intravenously injected in a dose of 16 mg/kg. After 24 hr, each tissue was sampled in the same manner as in Test Example 5 and the concentration of the metal ion was measured through ICP-MS (Varian 800-MS, Palo Alto, US).

The results of ICP-MS of the concentration of the iron ion accumulating in normal tissue and tumorous tissue after the administration of "iron ion-bound apotransferrin" (transferrin) to the tumor xenograft mice are shown in Table 6 below.

TABLE 6

|  | Saline | Transferrin | Fold increase |
|---|---|---|---|
| Tumor | 13.5 ± 1.34 | 43.9 ± 9.7 | 3.25 |
| Liver | 74.5 ± 7.5 | 94.7 ± 8.1 | 1.27 |
| Lung | 28.3 ± 6.1 | 43.9 ± 17.9 | 1.55 |
| Kidney | 56.9 ± 7.5 | 41.2 ± 1.7 | 0.72 |
| Heart | 32.2 ± 1.8 | 70.1 ± 12.3 | 2.18 |
| Muscle | 29.5 ± 4.2 | 25.7 ± 5.2 | 0.87 |
| Stomach | 27.8 ± 3.8 | 46.4 ± 14.9 | 1.67 |
| Brain | 22.5 ± 3.7 | 28.4 ± 3.5 | 1.26 |

As is apparent from Table 6, upon the administration of the iron ion-bound apotransferrin (transferrin), the concentration of the iron ion in tumorous tissue was increased 3.2-fold or more compared to the control, and was much higher than the extent of increase in the main organs such as the liver, kidneys, heart, stomach, brain and the like.

Example 1: Administration of Sensitizer for Thermal Therapy and Thermal Cancer Therapy Using Electromagnetic Waves In order to continue abnormal division, cancer cells receive large amounts of the nutrients necessary for rapid cell division but exhibit decreased metabolic control performance. Although cancer cells actually over-express the transferrin receptor and thus receive a large amount of iron, which is necessary for cell cleavage, they are known to be relatively sensitive to high heat due to their inferior thermal control capability compared to normal cells. Hence, when heat is intensively applied only to the cancer cells, it is possible to selectively kill the cancer cells. The transferrin that targets cancer cells functions to intensively deliver iron to the cancer cells by means of the transferrin receptor, which is over-expressed in cancer cells. As such, when the cancer cells are irradiated with electromagnetic waves, the cancer cells are expected to be killed due to the temperature elevation.

In Example 1, the metal ion-bound material, confirmed to have superior temperature elevation in the test examples, was used as a sensitizer for thermal therapy, and potential anticancer effects were evaluated upon thermal treatment of the tumor xenograft animal model.

To this end, a lung cancer cell line NCI-H460-luc2 (Califer Life Sciences) was cultured, and 5×10$^6$ cells were subcutaneously injected into 6 to 8-week-old female BALB/c athymic nude mice (Damul Science), and the mice were bred for about 10 days so as to grow tumorous tissue to a size of 100 mm$^3$ or more, yielding the tumor xenograft animal models for the evaluation of cancer treatment effects.

As the sensitizing composition for thermal therapy, iron sucrose was prepared in the same manner as in Test Example 1, and 0.1 ml of the iron sucrose aqueous solution having a concentration of 0.2 mg/ml was intravenously injected into the established tumor xenograft mice so as to reach a dose of 1 mg/kg.

As the sensitizing composition for thermal therapy, "iron ion-bound apotransferrin" (transferrin) was prepared in the same manner as in Test Example 3, and 0.1 ml of the transferrin aqueous solution having a concentration of 5 mg/ml was intravenously injected into the established tumor xenograft mice so as to reach a dose of 20 mg/kg.

As the control, saline was administered. 4 hr after administration, electromagnetic waves were applied in an energy dose of 100 W for 3 min using a radio-frequency hyperthermia system (EHY-2000, Oncothermia), and the temperatures of normal tissue and tumorous tissue were measured using a thermal imaging device (E60, Korea Rental, Korea). The results are shown in FIGS. 9 to 11.

As illustrated in FIGS. 9 to 11, in the control, there was no difference between normal tissue and tumorous tissue because the temperatures of normal tissue and tumorous tissue were increased by about 1° C. before and after the application of electromagnetic waves. However, in the group to which iron sucrose was administered, changes in the temperature before and after the application of electromagnetic waves were 1° C. for normal tissue and 1.9° C. for tumorous tissue. In the group to which iron ion-bound apotransferrin (transferrin) was administered, changes in the temperature before and after the application of electromagnetic waves were 1° C. for normal tissue and 2° C. for tumorous tissue. As seen in FIGS. 9 to 11, when the tumorous tissue of the mice to which the sensitizer for thermal therapy was administered was irradiated with electromagnetic waves, the temperature was elevated in the tumorous tissue more than in the normal tissue, resulting from the generation of heat in the iron ion delivered to the tumorous tissue.

Next, the potential to treat cancer was evaluated using the metal ion-bound material as the sensitizer upon thermal therapy. A lung cancer cell line NCI-H460-luc2 (Califer Life Sciences) was cultured, and 5×10$^6$ cells were subcutaneously injected into 6 to 8-week-old female BALB/c athymic nude mice (Damul Science), and the mice were bred for about 10 days so as to grow tumorous tissue to a size of 100 mm$^3$ or more, yielding the tumor xenograft animal models for the evaluation of cancer treatment effects.

As the sensitizing composition for thermal therapy, the metal ion-bound material was prepared in the manner of Test Example 1, and the established tumor xenograft mice were intravenously injected with 0.1 ml of each of the metal ion-monosaccharide bound material (iron gluconate), metal ion-disaccharide bound material (iron sucrose), metal ion-oligosaccharide bound material (iron isomaltoside), and metal ion-polysaccharide bound materials (iron carboxymaltose, iron dextran, iron starch) so as to reach a dose of 1 mg/kg.

Also, the sensitizing composition for thermal therapy, that is, the iron ion-bound apotransferrin (transferrin), was prepared in the manner of Test Example 3, and 0.1 ml thereof was intravenously injected into the established tumor xenograft mice so as to reach a dose of 20 mg/kg.

After 4 hr, thermal treatment was performed three times per week for a total of four weeks using a radio-frequency hyperthermia system (EHY-2000, Oncothermia) with an energy dose of 100 W for 10 min. As such, a non-treated group and a saline-treated group were set as controls. In order to analyze the size of tumorous tissue in the last week, bioluminescence imaging was performed. For bioluminescence of a luciferase-expressing cancer cell line NCI-H460-luc2, D-luciferin (Xenogen, USA) was intraperitoneally injected at a concentration of 150 mg luciferin/kg/d into the mice, the mice were anesthetized through inhalation using a mixture of isoflurane gas and oxygen, and luminous cancer cells were subjected to overlap photographing using a Xenogen imager (IVIS 200), and analyzed using Igor Pro imaging analysis software. The results are shown in FIG. 12.

FIG. 12 illustrates the results of bioluminescence imaging of the size of the tumorous tissue in the mouse models following radio-frequency thermal therapy after the administration of the tumor xenograft mouse models of Example 1 with nothing (A), saline (B), iron gluconate (C), iron sucrose (D), iron carboxymaltose (E), iron dextran (F), iron starch (G) and transferrin (H).

As illustrated in FIG. 12, unlike the non-treated group (A) and the saline-treated group (B), the groups to which the metal ion-bound materials were administered (C to H) were measured for a reduction in the size of cancer after thermal therapy. In particular, in the groups to which iron sucrose (D), iron dextran (F) and transferrin (H) were administered, the cancer treatment effects through thermal therapy were excellent.

Also, when using iron sucrose, iron dextran and transferrin, which were confirmed to have outstanding anticancer effects as the sensitizer for thermal therapy, the potential to cure cancer was evaluated upon thermal treatment using electromagnetic waves. To this end, saline, iron dextran, iron sucrose, and iron ion-bound apotransferrin (transferrin) aqueous solutions were intravenously injected every other day three times per week into the tumor xenograft BALB/c athymic nude mice. After 4 hr, thermal treatment for 30 min or more using a radio-frequency hyperthermia system (EHY-2000, Oncothermia) with an energy dose of 100 W was performed for a total of four weeks, and the size of tumorous tissue was monitored every week. In the groups to which iron dextran and iron sucrose were administered, 0.1 ml of iron dextran or iron sucrose aqueous solution having a concentration of 0.2 mg/ml was intravenously injected. In the group to which transferrin was administered, 0.1 ml of the transferrin aqueous solution having a concentration of 5 mg/ml was intravenously injected. As such, the non-treated group and the saline-treated group were used as controls.

In order to analyze the size of tumorous tissue, bioluminescence imaging was regularly performed at an interval of one week, and analysis was performed using Igor Pro imaging analysis software. The results are shown in FIG. 13.

As illustrated in FIG. 13, based on the results of comparison of the initial size of tumorous tissue and the size of tumorous tissue after four weeks through bioluminescence imaging, the growth of cancer was initially slightly inhibited in the saline-treated group compared to the non-treated group, but the effects were reduced over time. In the test groups to which iron dextran and iron sucrose were respectively administered as sensitizers, the rate of growth of cancer was significantly reduced upon thermal treatment using electromagnetic waves. In the group to which transferring was administered, the growth of cancer was remarkably inhibited, and the cancer was reduced in size and then disappeared completely after four weeks, at which time the test was terminated, thus exhibiting superior anticancer efficacy.

Although specific embodiments of the present invention have been disclosed in detail as described above, it is obvious to those skilled in the art that such description is merely of preferable exemplary embodiments and is not construed to limit the scope of the present invention. Therefore, the substantial scope of the present invention will be defined by the appended claims and equivalents thereof.

INDUSTRIAL APPLICABILITY

According to the present invention, the use of the sensitizing composition for thermal cancer therapy can selectively accumulate a metal component only in cancer cells, and thus this thermal therapy using the sensitizing composition is regarded as an ideal anticancer treatment method without pain or side effects and is expected to be widely useful in anticancer treatment. Furthermore, this thermal cancer therapy can be used in combination with chemotherapy, radiation therapy, etc., thus increasing the potential to cure cancer.

The invention claimed is:

1. A method of treating an animal subject with cancer, consisting of:
    (a) administering a composition to the animal subject, wherein the composition consists of
        (i) a sensitizer which is a metal ion-carbohydrate complex in which (i-a) a metal ion selected from the group consisting of an iron ion and a magnesium ion is noncovalently bound to (i-b) a carbohydrate selected from the group consisting of carboxymaltose, isomaltoside, and starch; and
        (ii) water as a pharmaceutically acceptable carrier, and
    wherein the administering the composition results in localization of the metal ion of the metal-carbonhydrate complex in a cancerous tissue of the animal; and
    (b) applying electromagnetic waves to the animal subject thereby generating amplified heat at cancerous tissue compared to non-cancerous tissues,
    wherein the applying electromagnetic waves causes a decrease in a size of cancerous mass of the cancerous tissue.

2. The method according to claim 1, wherein the sensitizer is administered in a dose of 0.1 to 50 mg/kg.

3. The method according to claim 1, wherein the electromagnetic waves are selected from the group consisting of gamma rays, X-rays, UV rays, visible light, IR light, microwaves, and radio waves.

4. The method according to claim 1, wherein the method is performed in combination with one or more therapy selected from the group consisting of chemotherapy, radiation therapy, biological therapy, immunotherapy, and photodynamic therapy.

* * * * *